United States Patent
Ishikawa et al.

(10) Patent No.: US 10,390,126 B2
(45) Date of Patent: Aug. 20, 2019

(54) EARPHONE FOR AUDIOMETER, AND AUDIOMETER

(71) Applicant: RION Co., Ltd., Tokyo (JP)

(72) Inventors: Shinichi Ishikawa, Tokyo (JP); Ryoichi Hamanaka, Tokyo (JP); Kaori Sato, Tokyo (JP)

(73) Assignee: RION Co., Ltd., Tokyo (JP)

( * ) Notice: Subject to any disclaimer, the term of this patent is extended or adjusted under 35 U.S.C. 154(b) by 0 days.

(21) Appl. No.: 16/134,150

(22) Filed: Sep. 18, 2018

(65) Prior Publication Data

US 2019/0116413 A1    Apr. 18, 2019

(30) Foreign Application Priority Data

Oct. 12, 2017  (JP) .................. 2017-198372

(51) Int. Cl.
| | |
|---|---|
| *H04R 1/10* | (2006.01) |
| *H04R 29/00* | (2006.01) |
| *A61B 5/00* | (2006.01) |
| *A61B 5/12* | (2006.01) |
| *G01H 3/00* | (2006.01) |

(52) U.S. Cl.
CPC ............ *H04R 1/1041* (2013.01); *A61B 5/12* (2013.01); *A61B 5/123* (2013.01); *A61B 5/486* (2013.01); *A61B 5/6803* (2013.01); *A61B 5/7465* (2013.01); *G01H 3/00* (2013.01); *H04R 1/10* (2013.01); *H04R 1/105* (2013.01); *H04R 1/1008* (2013.01); *H04R 1/1091* (2013.01); *H04R 29/00* (2013.01); *H04R 29/008* (2013.01); *A61B 5/721* (2013.01); *A61B 5/7264* (2013.01); *A61B 2560/0214* (2013.01); *H04R 2420/07* (2013.01)

(58) Field of Classification Search
CPC .... H04R 1/1041; H04R 1/1008; H04R 1/105; H04R 1/1091; H04R 2420/07; G01H 3/00
USPC ...................................... 381/74, 58; 600/559
See application file for complete search history.

(56) References Cited

U.S. PATENT DOCUMENTS

| | | |
|---|---|---|
| 4,107,465 A | 8/1978 | Charlebois et al. |
| 5,197,332 A | 3/1993 | Shennib |

(Continued)

FOREIGN PATENT DOCUMENTS

| | | |
|---|---|---|
| JP | H09308620 | 12/1997 |
| JP | H10085202 A | 4/1998 |

(Continued)

OTHER PUBLICATIONS

Decision to Grant dated Feb. 22, 2018 for the corresponding Japanese Patent Application No. 2017-198372.

(Continued)

*Primary Examiner* — Xu Mei
*Assistant Examiner* — Ammar T Hamid
(74) *Attorney, Agent, or Firm* — Rankin, Hill & Clark LLP

(57) ABSTRACT

An earphone for an audiometer is provided, which includes a right earphone portion, a left earphone portion, a right light-emitter corresponding to the right earphone portion, a left light-emitter corresponding to the left earphone portion, and a controller, wherein the controller selects any one of the right earphone portion and the left earphone portion as an earphone portion for presenting a test sound, and causes the light-emitter corresponding to the selected earphone portion to emit light in a mode in accordance with the test sound.

6 Claims, 8 Drawing Sheets

| STATE | | LIGHT-EMITTING MODE |
|---|---|---|
| COMMUNICATION ESTABLISHED | | FLASHING WITH BLUE |
| PRESENTING SIDE | PRESENTING | FIRST LEVEL RANGE: RED<br>SECOND LEVEL RANGE: YELLOW<br>THIRD LEVEL RANGE: GREEN |
| | NON-PRESENTING | WHITE |
| NON-PRESENTING SIDE | RESPONDING | ORANGE |
| | NON-RESPONDING | WHITE |

(56) References Cited

U.S. PATENT DOCUMENTS

| | | | | |
|---|---|---|---|---|
| 2002/0165466 A1* | 11/2002 | Givens | .................. | A61B 5/121 |
| | | | | 600/559 |
| 2009/0013787 A1 | 1/2009 | Esnouf | | |
| 2011/0230786 A1* | 9/2011 | Esnouf | .................. | A61B 5/121 |
| | | | | 600/559 |
| 2017/0195770 A1* | 7/2017 | Cheney | ................ | H04R 1/1025 |

FOREIGN PATENT DOCUMENTS

| | | |
|---|---|---|
| JP | 6126289 B1 | 5/2017 |
| WO | 2005/096940 A1 | 10/2005 |
| WO | 2010/031134 A1 | 3/2010 |

OTHER PUBLICATIONS

Partial European Search Report dated Feb. 15, 2019 for the corresponding European Patent Application No. 18198920.3.

* cited by examiner

*FIG. 6*

| STATE | | LIGHT-EMITTING MODE |
|---|---|---|
| COMMUNICATION ESTABLISHED | | FLASHING WITH BLUE |
| PRESENTING SIDE | PRESENTING | FIRST LEVEL RANGE: RED<br>SECOND LEVEL RANGE: YELLOW<br>THIRD LEVEL RANGE: GREEN |
| | NON-PRESENTING | WHITE |
| NON-PRESENTING SIDE | RESPONDING | ORANGE |
| | NON-RESPONDING | WHITE |

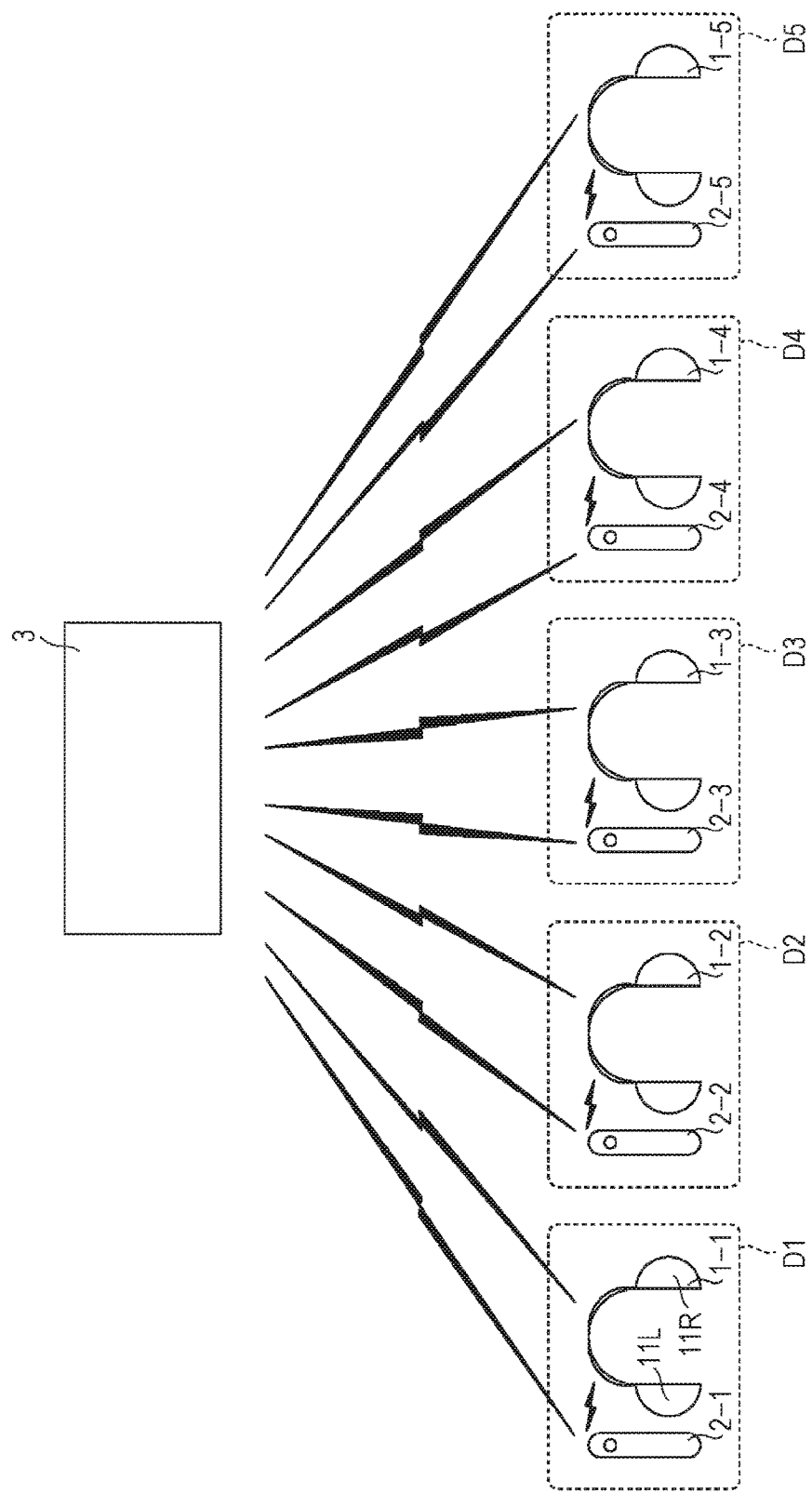

EARPHONE FOR AUDIOMETER, AND AUDIOMETER

CROSS-REFERENCE TO RELATED APPLICATION

This application claims priority from Japanese Patent Application No. 2017-198372 filed with the Japan Patent Office on Oct. 12, 2017, the entire contents of which are hereby incorporated by reference.

BACKGROUND

1. Technical Field

The present disclosure relates to an earphone for an audiometer, and the audiometer.

2. Related Art

Generally, in the audiometry using an audiometer, an examiner operates an audiometer main body for presenting a test sound to a subject by an earphone. Then, the examiner monitors a progress status of examination, a response to the test sound by the subject, and an examination result through a display of the audiometer main body. In addition, in the audiometry, the test sound is controlled to be presented or not presented by the audiometer according to an automatic audiometry program. At this time, whether the test sound is presented or not is checked by a test sound presenting lamp, or the like, of the audiometer main body. Then, it is necessary that ambient noises be sufficiently small. In particular, in the case of a screening audiometry in which an audiometry room is not used, it is important to check an ambient noise level. Therefore, an environmental noise monitor may be equipped in the audiometer main body.

In a wired audiometer, the earphone and the audiometer main body are connected by a cable. On the other hand, a wireless audiometer is also received a lot of attention, including an earphone and an audiometer main body which communicate with each other in a wireless manner (for example, see JP 6126289 B1).

A certain audiometer includes a light-emitting diode (LED) which is provided in the center portion of a headset case. Then, the LED tells an operator (examiner) about the operating state such as a remaining capacity or a charged capacity of a battery (for example, see U.S. Pat. No. 5,197,332).

SUMMARY

An earphone for an audiometer of the present disclosure includes a right earphone portion, a left earphone portion, a right light-emitter corresponding to the right earphone portion, a left light-emitter corresponding to the left earphone portion, and a controller, wherein the controller selects any one of the right earphone portion and the left earphone portion as an earphone portion for presenting a test sound, and causes the light-emitter corresponding to the selected earphone portion to emit light in a mode in accordance with the test sound.

BRIEF DESCRIPTION OF DRAWINGS

FIG. 6 is a table illustrating an example of light-emitting modes of a right light-emitter 13R and the left light-emitter 13L in the first embodiment;

FIG. 9 is a diagram illustrating a configuration of an audiometer according to a second embodiment of the present disclosure.

DETAILED DESCRIPTION

Figure 1:
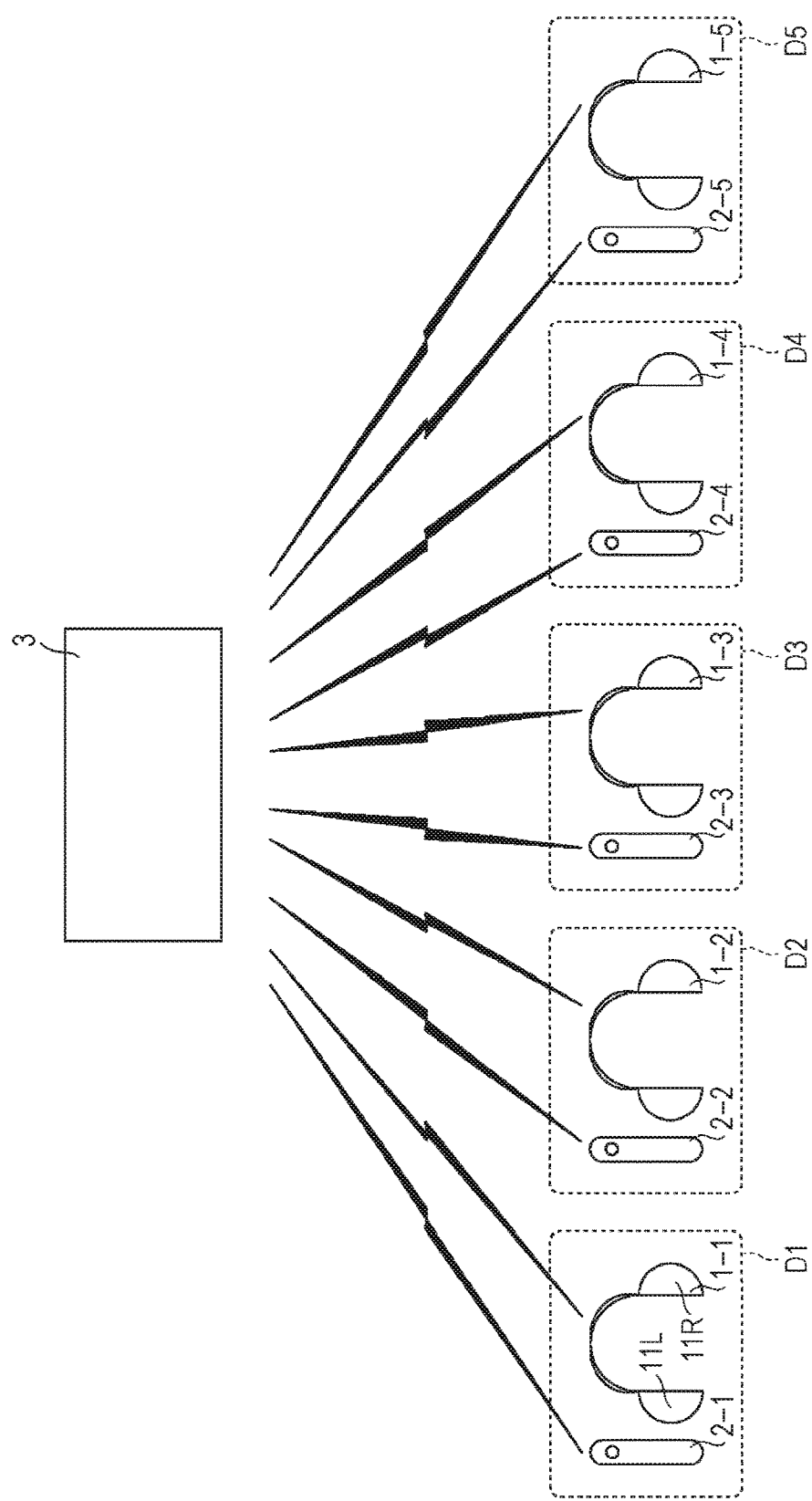
FIG. 1 is a diagram illustrating a configuration of an audiometer according to a first embodiment of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In the audiometer described above, an operator receives information such like the operating states with an LED of the headset. However, it is not easy for the operator to monitor the progress of the examination only with the LED of the headset.

In the case of a wireless audiometer, it is considered that the examiner visually checks the state of the subject at a position separated further from the subject compared to a wired audiometer. Therefore, it is not easy for the examiner to monitor the progress of the examination.

In particular, in the case of an automatic audiometry, the audiometry may be performed on plural subjects at the same time. At that time, in an audiometer configured to check, with the audiometer main body, a response or non-response by the subject against an ON or OFF state of a test sound, it is not easy to check both the displaying of the main body and the response conditions of the subjects. Therefore, the progress status of the automatic audiometry of each subject is hard to monitor.

In addition, normally, an environmental noise level to be monitored is necessarily measured near the subject. Therefore, in a case where the subject is located at a position separated from the audiometer body, and an environmental noise monitors installed in the audiometer body, the noise level of the vicinity of the subject may not be measured with accuracy.

The audiometer of the present disclosure has been developed for the purpose of overcoming the above problems. In other words, an object of the present disclosure is to provide an earphone for an audiometer, and the audiometer with which an examiner easily monitor whether an audiometry progresses properly.

An earphone for an audiometer according to the present disclosure, including a right earphone portion, a left earphone portion, a right light-emitter corresponding to the right earphone portion, a left light-emitter corresponding to the left earphone portion, and a controller, wherein the controller selects any one of the right earphone portion and the left earphone portion as an earphone portion for presenting a test sound, and causes the light-emitter corresponding to the selected earphone portion to emit light in a mode in accordance with the test sound.

The earphone for an audiometer according to the present disclosure, may further includes a microphone (for example, for measuring an environmental noise or for a monitor of the test sound) which measures a sound pressure of the earphone portion, wherein the controller may cause the light-emitter corresponding to the selected earphone portion to emit light in a mode in accordance with the sound pressure measured by the microphone.

The audiometer according to the present disclosure includes an earphone for an audiometer described above, and a main body which causes the earphone for the audiometer to present a test sound.

According to the present disclosure, it is possible to provide the earphone for the audiometer, and the audiometer with which the examiner easily monitor whether an audiometry progresses nominally.

Hereinbelow, embodiments of the present disclosure will be described on the basis of the drawings.

First Embodiment

FIG. 1 is a diagram illustrating a configuration of the audiometer according to a first embodiment of the present disclosure. The audiometer illustrated in FIG. 1 includes a plurality of (herein, five) test devices Di (i=1, . . . , 5) and a main body 3. The test device Di includes an earphone 1-$i$ (i=1, . . . , 5) and a subject response device 2-$i$ (i=1, . . . , 5). One test device Di is assigned to one subject. The earphone 1-$i$ presents the test sound to the assigned subject. The subject response device 2-$i$ is operated by the subject when the subject assigned the test device Di hears the test sound. Herein, the earphone 1-$i$ is a circum-aural type earphone.

In the embodiment, the earphone 1-$i$ and the main body 3, the subject response device 2-$i$ and the main body 3, and the earphone 1-$i$ and the subject response device 2-$i$ are not connected by cables, and physically separated. The earphone 1-$i$ and the main body 3, and the subject response device 2-$i$ and the main body 3 are connected in a wireless communication manner. Therefore, the earphone 1-$i$, the subject response device 2-$i$, and the main body 3 each include independent power sources. The earphone 1-$i$ and the subject response device 2-$i$ are not connected with a power source cable. The audiometry may be conducted with batteries as the power sources for the earphone 1-$i$ and the subject response device 2-$i$ for the audiometry.

The main body 3 performs a wireless communication with the earphone 1-$i$. Further, independently of the wireless communication with the earphone 1-$i$, the main body 3 performs a wireless communication with the subject response device 2-$i$. In the first embodiment, the main body 3 sends a test sound output command to the earphone 1-$i$ to cause the earphone 1-$i$ to emit the test sound. Further, the main body 3 acquires information of a subject's operation (operation information of the subject response device 2-$i$) on the subject response device 2-$i$. For example, the main body 3 independently performs a wireless communication with the earphone 1-$i$ and the subject response device 2-$i$ of the test device Di in a time division multiplexing system.

Specifically, the test sound output command is transmitted to all the earphones 1-1 to 1-5 from the main body 3 in a specific time slot among a predetermined number of time slots in one frame. In addition, the operation information of all the subject response devices 2-1 to 2-5 is sequentially transmitted from the subject response devices 2-1 to 2-5 to the main body 3 in a plurality of specific time slots among the predetermined number of slots. Sound pressure levels and frequencies of the test sounds of a left earphone portion 11L and/or a right earphone portion 11R are designated by the test sound output command.

The earphone 1-$i$ generates a test sound signal designated by the test sound output command. The generated test sound is presented to the subject by the earphone 1-$i$. In this way, the test sound signal (audio signal) is generated by the earphone 1-$i$. Therefore, noises caused by wireless communication are hardly superimposed on the test sound signal.

Figure 2:
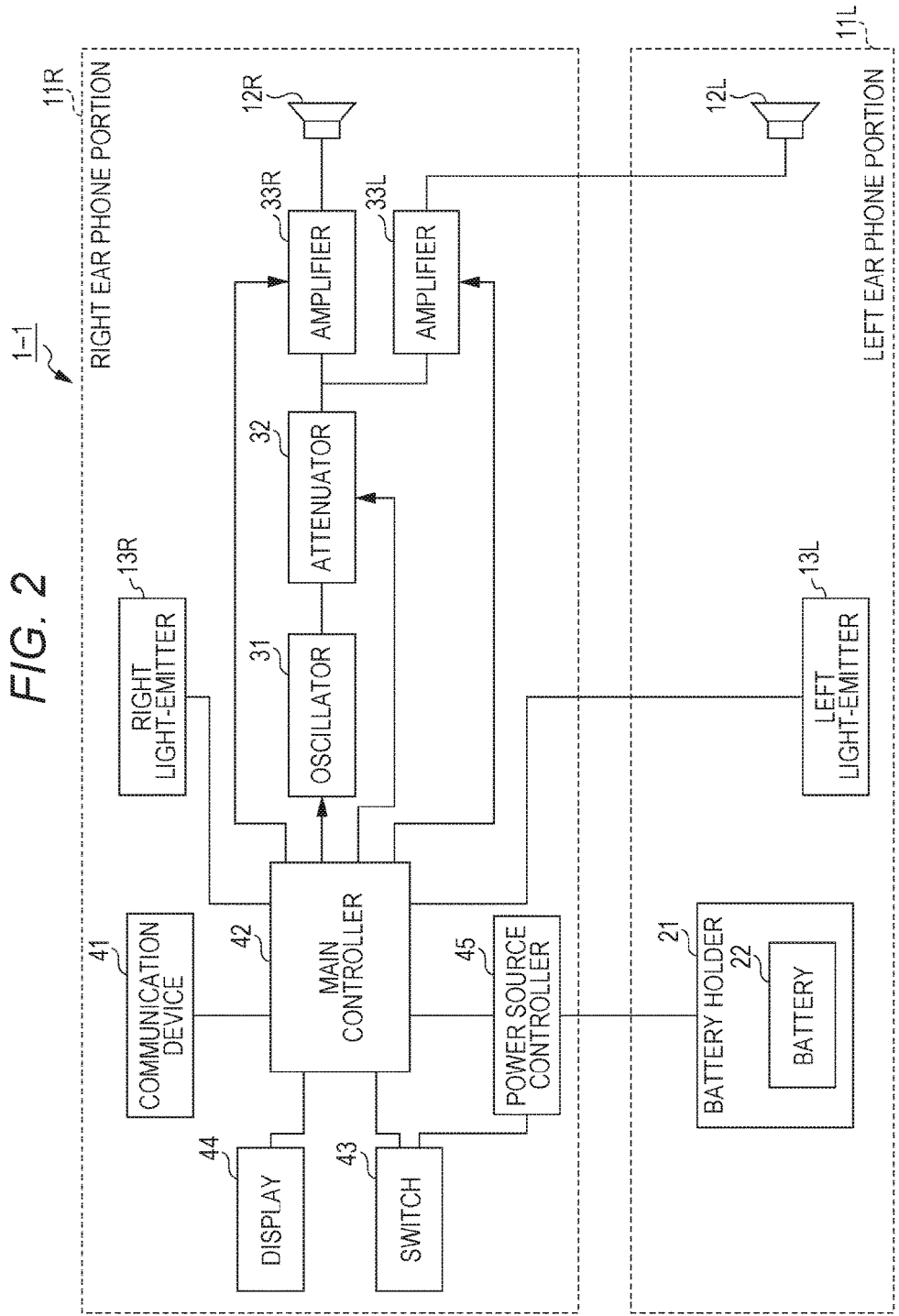
FIG. 2 is a block diagram illustrating a configuration of an earphone 1-1 in FIG. 1.
Figure 3:
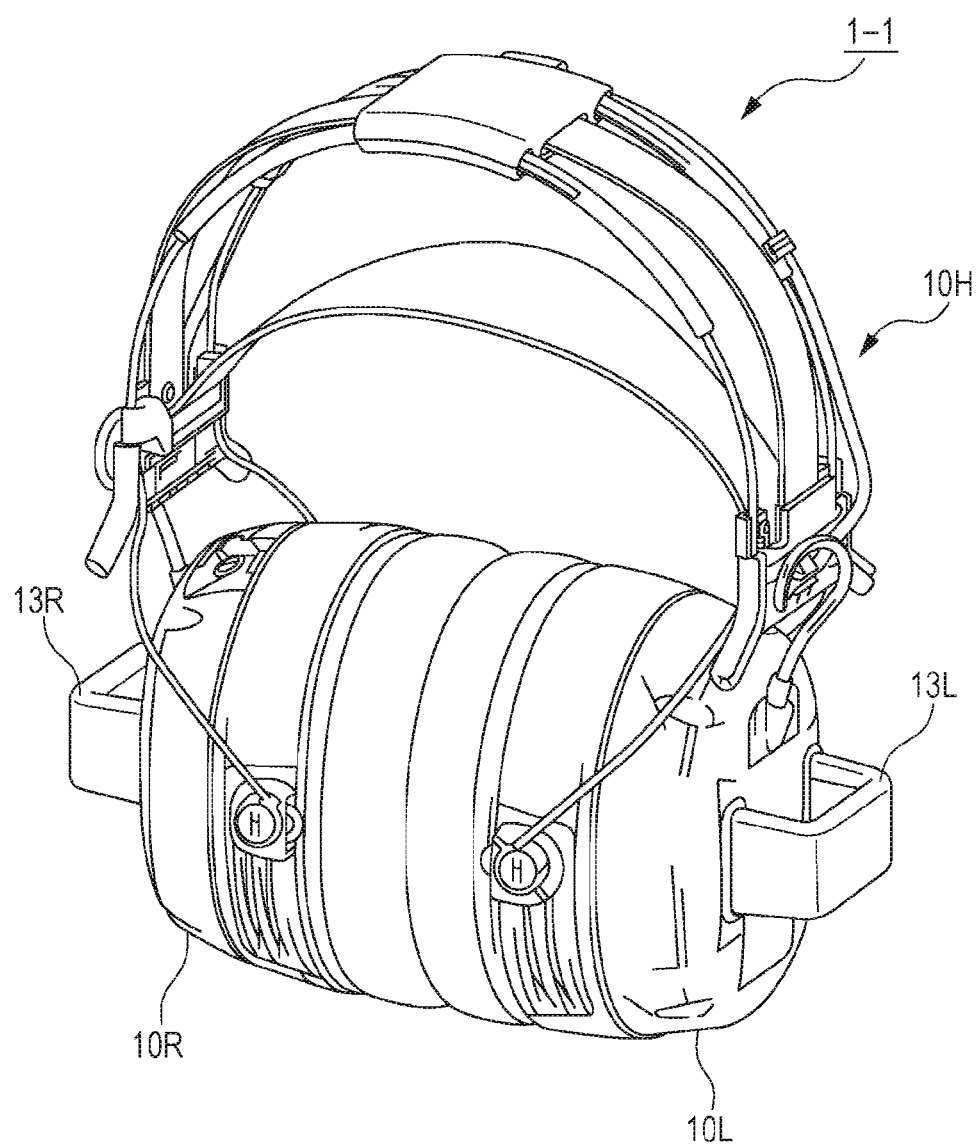
FIG. 3 is a perspective view illustrating an example of the earphone 1-1 in FIG. 1.

FIG. 2 is a block diagram illustrating a configuration of the earphone 1-1 in FIG. 1. FIG. 3 is a perspective view illustrating an example of the earphone 1-1 in FIG. 1. As illustrated in FIGS. 2 and 3, the earphone 1-1 includes the left earphone portion 11L equipped with a left casing 10L, the right earphone portion 11R equipped with a right casing 10R, and a headband portion 10H which connects the left casing 10L and the right casing 10R.

The left earphone portion 11L includes a speaker 12L. The speaker 12L presents the test sound to the left ear of the subject. The right earphone portion 11R includes a speaker 12R. The speaker 12R presents the test sound to the right ear of the subject. In addition, the left light-emitter 13L is provided in correspondence with the left earphone portion 11L. The right light-emitter 13R is provided in correspondence with the right earphone portion 11R. The right light-emitter 13R and the left light-emitter 13L each emit light in a predetermined mode (displaying color, blinking pattern, etc.) according to a progress of the audiometry.

In the embodiment, the left light-emitter 13L includes a left light-emitting element (for example, LED) which is provided in a left hook portion of the left earphone portion 11L. In addition, the right light-emitter 13R includes a right light-emitting element (for example, LED) which is provided in a right hook portion of the right earphone portion 11R.

Figure 4:
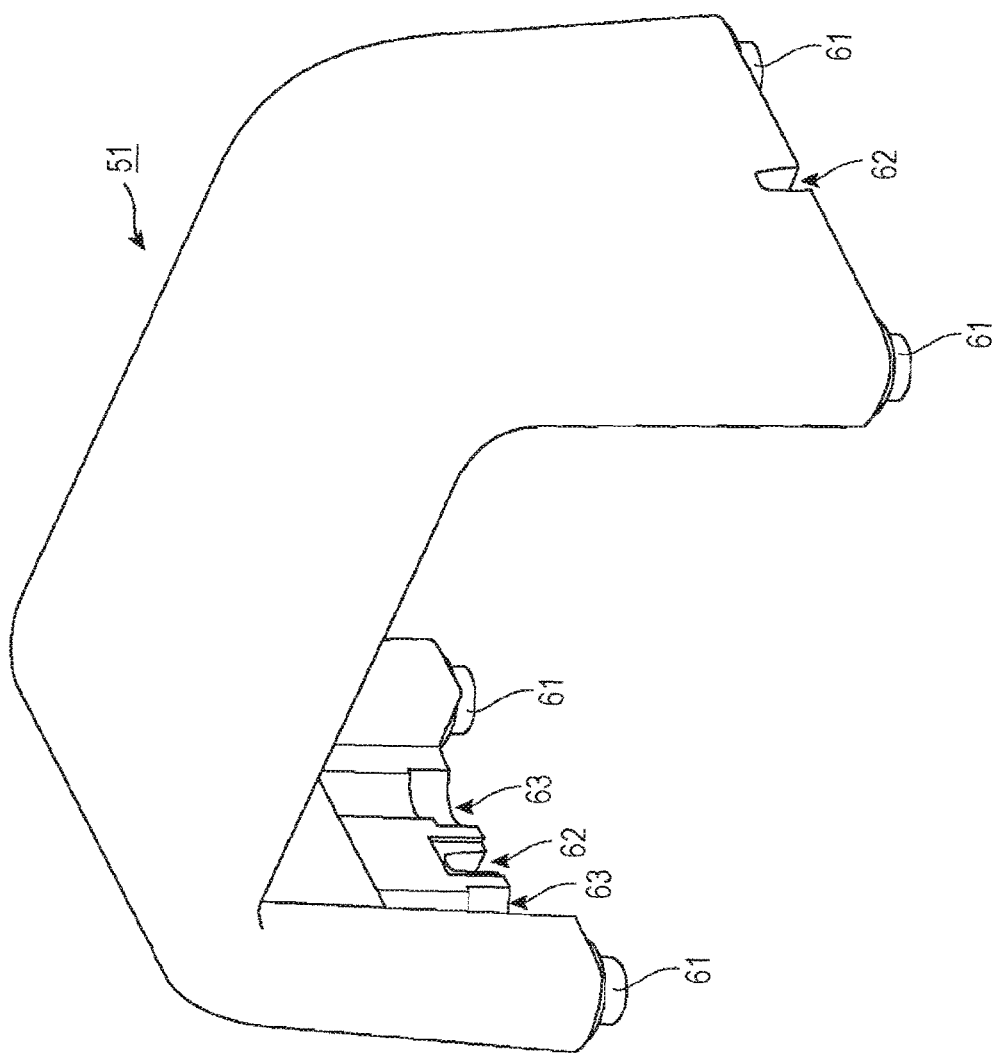
FIG. 4 is a perspective view illustrating components of a left light-emitter 13L in FIGS. 2 and 3 (1/2)
Figure 5:
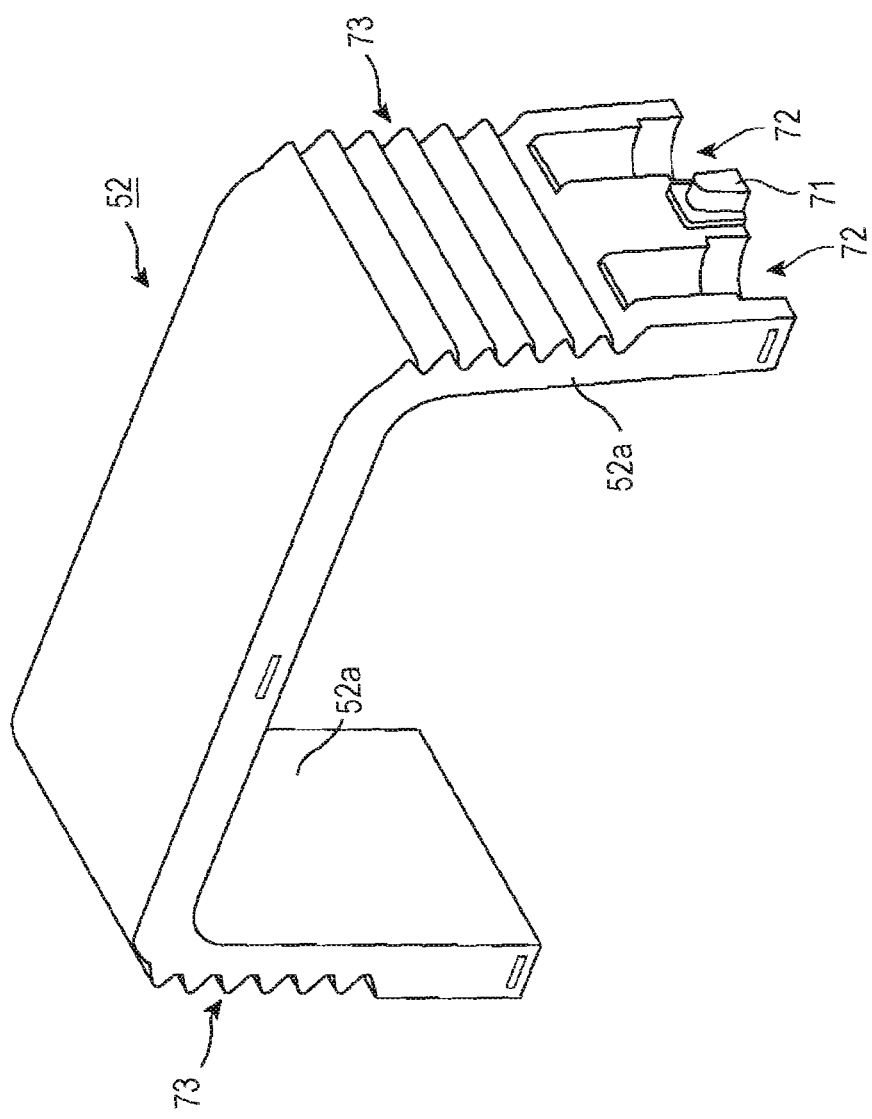
FIG. 5 is a perspective view illustrating components of the left light-emitter 13L in FIGS. 2 and 3 (2/2)

FIGS. 4 and 5 are perspective views illustrating components of the left light-emitter 13L in FIGS. 2 and 3. Further, the right light-emitter 13R also includes a similar configuration to the left light-emitter 13L.

The left light-emitter 13L includes an outer member 51 illustrated in FIG. 4 and the inner member 52 illustrated in FIG. 5. The inner member 52 is fixed to the inside of the outer member 51.

The outer member 51 and the inner member 52 each have a bended plate shape, and are made of a transparent or translucent material (for example, resin such as PETG or acrylic).

As illustrated in FIG. 4, the outer member 51 includes a leg portion 61, a groove 62, and a recess 63 at both ends of the plate shape. The lea portion 61 is a portion which is connected to the left casing 10L. The groove 62 is a groove which is used for the inner member 52 to be positioned and reinforced when it is fixed to the outer member 51. In the recess 63, the light-emitting element is disposed. Further, a fine rugged pattern may be formed on the surface by blasting and emboss processing. With this configuration, the light irregularly reflected on a light-diffusing portion 73 (described below) can be further diffused. Therefore, the light emitted from the light-emitting element is visible from various directions (including a direction of the examiner).

In addition, as illustrated in FIG. 5, the inner member 52 includes a projection 71 and a recess 72 at both ends of the plate shape, and further includes the light-diffusing portion 73 in a side surface 52$a$. The projection 71 is a projection which is used for the inner member 52 to be positioned and reinforced when it is fixed to the outer member 51. The projection 71 is disposed in the inner portion of the groove 62. The recess 72 is disposed to face the recess 63. An approximately cylindrical hole is formed by the recess 72 and the recess 63. In the hole, the left light-emitting element is disposed. A part of the surface (outside surface) of the light-diffusing portion 73 is formed in a wave shape. With this configuration, the light emitted from the left light-emitting element is irregularly reflected on the light-diffusing portion 73. As a result, the light emitted from the left light-emitting element is visible from various directions (including a direction of the examiner).

In FIG. 2, the embodiment will be further described. The left earphone portion 11L further includes a battery holder 21. In the battery holder 21, a battery 22 (a primary battery or a secondary battery) is set.

In addition, in the embodiment, the right earphone portion 11R further includes an oscillator 31, an attenuator 32, an amplifier 33L for the left speaker 12L, and an amplifier 33R for the right speaker 12R.

The oscillator 31 is a circuit which oscillates a frequency signal designated by a control signal, and outputs the signal as the test sound signal. The attenuator 32 is a circuit which attenuates an amplitude of the test sound signal output from the oscillator 31 at a damping rate designated by the control signal. The amplifier 33L and the amplifier 33R each are circuits which amplify the amplitude of the test sound signal output from the oscillator 31 at an amplitude rate designated by the control signal.

Further, in the embodiment, the earphone 1-1 includes a communication device 41, a main controller 42, a switch 43, a display 44, and a power source controller 45.

The communication device 41 includes a communication circuit and an antenna. The communication device 41 performs the above wireless communication to receive and supply the test sound output command to the main controller 42. Further, the communication device 41 transmits voltage information and output sound information of the earphone 1-1 which are supplied from the main controller 42. Here, in the example of the output sound information, there are included the levels and frequencies of the output sounds of the earphone portions 11L and 11R, the examined ear (right or left), intermittency or continuity of the test sound output, ON or OFF state of the test sound according to the test sound output command (that is, ON or OFF state of a test sound presenting switch of the main body 3), noise setting (noise output or noise stop), and presence/absence of communication error detection.

The main controller 42 supplies the control signal corresponding to the test sound output command to the oscillator 31, the attenuator 32, and the amplifiers 33L and 33R. With this configuration, the test sound signal (the test sound signal having the designated frequency and the sound pressure level) designated by the test sound output command is output by the main controller 42 to the speaker 12L or the speaker 12R. In this way, the test sound is output from the speaker 12L or the speaker 12R by the main controller 42. Further, in a case where the test sound signal is supplied from the amplifier 33L to the speaker 12L, the test sound signal is supplied from the amplifier 33L to the speaker 12L via a signal cable which is disposed through the headband portion.

Furthermore, the main controller 42 independently controls the right light-emitter 13R and the left light-emitter 13L. Then, the main controller 42 causes each of the light-emitters to emit light at a predetermined mode according to the progress of the audiometry.

In particular, the main controller 42 performs
(a) an operation of selecting any one of the right earphone portion 11R and the left earphone portion 11L as the earphone portion for presenting the test sound, and
(b) an operation of causing a light-emitter (for example, the right light-emitter 13R in a case where the right earphone portion 11R is selected) to emit light in accordance with the selected earphone portion in a mode corresponding to a level of the test sound.

In addition, when the subject response device 2-1 detects a response to the test sound by the subject, the main controller 42 causes the right light-emitter 13R or the left light-emitter 13L, whichever corresponds to the unselected earphone portion, to emit light (for example, the left light-emitter 13L emits light when the right earphone portion 11R is selected). The light is emitted in a mode different from the mode used at the level of the test sound.

FIG. 6 is a table illustrating an example of the light-emitting modes of the right light-emitter 13R and the left light-emitter 13L in the first embodiment.

The main controller 42 independently causes the right light-emitter 13R and the left light-emitter 13L to emit light, for example, lighting or blinking as illustrated in FIG. 6.

For example, the main controller 42 makes at least one of the right light-emitter 13R and the left light-emitter 13L blinking with a blue color during a predetermined time when the communication with the main body 3 is established.

In addition, with respect to the selected earphone portion, which presents the test sound, the main controller 42 makes the light-emitter (the right light-emitter 13R or the left light-emitter 13L) light with a color in accordance with the level of the test sound while the test sound is presented. For example, as illustrated in FIG. 6, the main controller 42 makes the light-emitter light with a red color in a case where the test sound level falls within a first level range (for example, a range higher than 110 dBHL), yellow in a case where the test sound level falls within a second level range (for example, a range of 110 dBHL or less and more than 90 dBHL), and green in a case where the test sound level falls within a third level range (for example, a range of 90 dBHL or less). In addition, the main controller 42 makes the light-emitter light with a white color while the test sound is not presented by the selected earphone portion.

On the other hand, with respect to the unselected earphone portion, which does not present the test sound, the main controller 42 makes the light-emitter (the right light-emitter 13R or the left light-emitter 13L) light with an orange color while the response to the test sound by the subject is detected. In addition, the main controller 42 makes the light-emitter of the unselected earphone portion light with a white color while the response to the test sound by the subject is not detected. Further, the corresponding subject response device 2-1 notifies the examiner, directly or through the main body 3, of a response or non-response to the test sound by the subject.

Therefore, after the earphone 1-1 is powered on, the right light-emitter 13R and the left light-emitter 13L both light with a white color before the examination starts (except a period when the communication is established).

Further, the main controller 42 is realized by a microcomputer or a digital signal processor for example.

In FIG. 2, the switch 43 is a switch which accepts an operation to activate the earphone 1-1. The display 44 is an indicator to indicate an operation status, for example, a status in which the earphone 1-1 is powered on or off.

The power source controller 45 is electrically connected to the battery holder 21 (that is, the battery 22) through the headband portion. The power source controller 45 selects and switches an operation mode of the earphone 1-1 in accordance with an operation on the switch 43 and a communication state. Then, the power of the battery 22 is supplied by the power source controller 45 to an internal circuit (the right light-emitter 13R, the left light-emitter 13L, the communication device 41, the main controller 42, and the display 44) corresponding to the operation mode selected at that moment.

Further, the power source controller 45 measures the voltage of the battery 22. The voltage information including the measured voltage is supplied to the main controller 42. The main controller 42 supplies the voltage information to the communication device 41.

In this way, the earphone 1-1 operates with the power supplied from the battery 22 serving as a power source. Then, the power source controller 45 of the earphone 1-*i* of the test device Di measures the power source voltage of the power source (the battery 22) of the earphone 1-*i*. The voltage information including the measured source voltage of the earphone 1-*i* is repeatedly and sequentially transmitted at a period of a predetermined number of frames using one specific time slot in one frame.

In the embodiment, the battery holder 21 and the battery 22 are disposed in the left earphone portion 11L. However, the battery holder 21 and the battery 22 may be disposed in the right earphone portion 11R. In addition, in the embodiment, the oscillator 31, the attenuator 32, the amplifiers 33L and 33R, the communication device 41, the main controller 42, the switch 43, the display 44, and the power source controller 45 are disposed in the right earphone portion 11R. However, some or all of these components may be disposed in the left earphone portion 11L.

Further, the remaining earphones 1-2 to 1-5 are also configured similarly to the earphone 1-1.

Figure 7:
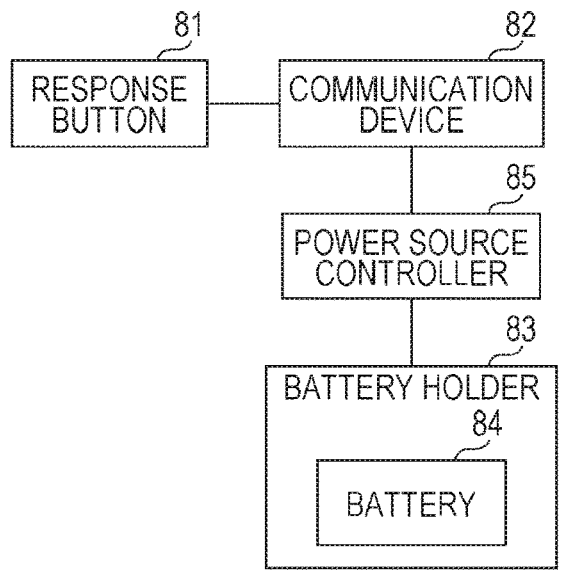
FIG. 7 is a block diagram illustrating a configuration of a subject response device 2-1 in FIG. 1.

FIG. 7 is a block diagram illustrating a configuration of the subject response device 2-1 in FIG. 1. As illustrated in FIG. 7, the subject response device 2-1 includes a response button 81 operated by the subject, a communication device 82, a battery holder 83 (and the battery 84 as the primary battery or the secondary battery set in the battery holder 83), and a power source controller 85.

For example, the response button 81 is a push-button switch which enters the ON state only when being pressed.

The communication device 82 includes a communication circuit and an antenna. The communication device 82 performs the wireless communication to transmit the operation information including the execution/non-execution of an operation on the response button 81 and the voltage information supplied by the power source controller 85.

The power source controller 85 is electrically connected to the battery holder 83 (that is, the battery 84). The power source controller 85 switches and selects operation modes of the subject response device 2-1 according to the operation on the response button 81 and a communication state. Then, the power of the battery 84 is supplied to an internal circuit (the communication device 82) corresponding to the operation mode selected at that moment by the power source controller 85. Further, the power source controller 85 measures the voltage of the battery 84. The voltage information including the measured voltage is supplied to the communication device 82.

Further, the remaining subject response devices 2-2 to 2-5 are also configured similarly to the subject response device 2-1.

Figure 8:
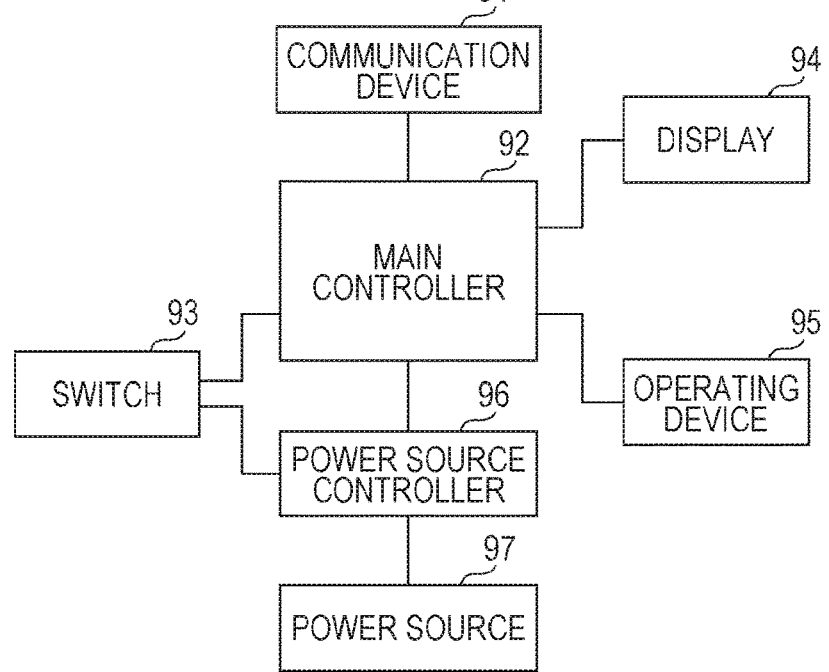
FIG. 8 is a block diagram illustrating a configuration of a main body 3 in FIG. 1.

FIG. 8 is a block diagram illustrating a configuration of the main body 3 in FIG. 1. As illustrated in FIG. 8, the main body 3 includes a communication device 91, a main controller 92, a switch 93, a display 94, an operation device 95, a power source controller 96, and a power source 97.

The communication device 91 includes a communication circuit and an antenna. The communication device 91 performs the wireless communication to transmit the test sound output command, and to receive the operation information and the voltage information.

The main controller 92 uses the communication device 91 to transmit the test sound output command to the earphones 1-1 to 1-5 of the plurality of test devices D1 to D5, and to receive the operation information from the subject response devices 2-1 to 2-5. With this configuration, the audiometry of plural subjects is performed by the main controller 92.

Further, the main controller 92 is realized by a microcomputer or a digital signal processor.

The switch 93 is a switch which is operated by the examiner in order to activate the main body 3.

The display 94 is an indicator or a liquid crystal display. A result (audiogram, or the like) of the audiometry is displayed in the display 94. The operation device 95 accepts an examiner's operation by a hard key or the like. The main controller 92 causes the communication device 91 to transmit the test sound output command according to the examiner's operation accepted by the operation device 95. Further, the main controller 92 causes the display 94 to display the result of the audiometry or the like on the basis of the operation information citation received by the communication device 91.

The power source controller 96 is electrically connected to the power source 97. The power source controller 96 switches and selects the operation modes of the main body 3 according to an operation on the switch 93 and a communication state. Then, the power from the power source 97 is supplied to an internal circuit (the communication device 91, the main controller 92, and the display 94) corresponding to the operation mode selected at that moment by the power source controller 96. The power source 97 is a power source circuit which generates DC power from the battery or the AC commercial power source.

Further, the wireless communication between the main body 3 and the earphone 1-*i* and the subject response device 2-*i* may be performed by a time division multiplexing method described in JP 6126289 B1 for example.

Further, in the embodiment, the number of test devices Di is "5". However, the number of test devices Di not limited to a specific number.

Next, an operation of the audiometer according to the first embodiment will be described.

First, the power source of the earphone 1-*i* used in the audiometry is turned on. When the power source is powered on, the main controller 42 of the earphone 1-*i* starts the light emission of the right light-emitter 13R and the left light-emitter 13L. At this time, the communication between the earphone 1-*i* and the main body 3 is not yet established. Therefore, the main controller 42 makes the right light-emitter 13R and the left light-emitter 13L light with a white white color.

On the other hand, when the power source turned on, the main body 3 detects the test device Di which exists within the wireless communication area. Further, for example, in the case illustrated in FIG. 1, the main body 3 can perform the audiometry using five test devices Di at maximum. In addition, the main body 3 may perform the audiometry using the test devices Di less than an upper limit value (here, 5).

In this case, when additional test devices Dj (j>i) are detected, the main body 3 adds the additional test devices Dj to the audiometry in the interval of wireless communication described in JP 6126289 B1.

At this time, the main controller 42 that has established the communication with the main body 3 makes the right light-emitter 13R and the left light-emitter 13L blinking with a blue color during a predetermined period of time. After the predetermined period of time has elapsed, the main controller 42 makes the right light-emitter 13R and the left light-emitter 13L light with a white color except at the time of presenting the test sound and at the time of detecting the response to the test sound by the subject.

Then, the main body 3 transmits the test sound output command designated by the examiner's operation on the operation device 95 or the test sound output command determined according to an automatic audiometry program to the earphone 1-*i* of the detected test device Di. When receiving the test sound output command, the main controller 42 of the earphone 1-*i* generates the test sound signal (audio signal) designated by the test sound output command. Then, the main controller 42 presents the test sound to the subject from the speaker (the speaker 12L of the left earphone portion 11L or the speaker 12R of the right earphone portion 11R) of the earphone portion which is designated by the test sound output command on the basis of the test sound signal. At this time, the main controller 42 makes the light-emitter (the right light-emitter 13R or the left light-emitter 13L) of the selected earphone portion, which presents the test sound, light with a color in accordance with the level of the test sound.

On the other hand, the subject response device 2-*i* monitors whether the subject presses the response button 81, and transmits the operation information which contains the execution/non-execution of the pressing of the response button 81. At this time, the corresponding earphone 1-*i* receives the operation information through the main body 3. While the response to the test sound by the subject is detected on the basis of the operation information, the main controller 42 of the earphone 1-*i* makes the light-emitter (the right light-emitter 13R or the left light-emitter 13L) of the unselected earphone portion, which does not present test sound, light with another color (orange).

As described above, according to the first embodiment, the earphone 1-*i* for the audiometer is provided with the right light-emitter 13R corresponding to the right earphone portion 11R and the left light-emitter 13L corresponding to the left earphone portion 11L. The main controller 42 selects any one of the right earphone portion 11R and the left earphone portion 11L as the earphone portion for presenting the test sound. Then, the main controller 42 causes the right light-emitter 13R or the left light-emitter 13L corresponding to the selected earphone portion to emit light in a mode in accordance with the level of the test sound.

With this configuration, the examiner can visually check the lighting state of the right light-emitter 13R and the left light-emitter 13L with almost no change in line of sight while looking at the subject's state. Therefore, the examiner easily monitors the normal progress of audiometry.

Second Embodiment

FIG. 9 is a diagram illustrating a configuration of the audiometer according to a second embodiment of the present disclosure. Further, the basic configurations and operations of the respective devices (the earphone 1-*i*, the subject response device 2-*i*, and the main body 3) in the audiometer according to the second embodiment are the same as those of the first embodiment except the following points.

In the second embodiment, the wireless communication is performed by the time division multiplexing system similarly to the first embodiment. However, in the first embodiment, the operation information and the voltage information transmitted by the subject response device 2-*i* are received by the main body 3. On the contrary, in the second embodiment, the operation information transmitted by the subject response device 2-*i* is received not by the main body 3 but by the corresponding earphone 1-*i*. Then, the voltage information transmitted by the subject response device 2-*i* is received by the corresponding earphone 1-*i* and the main body 3. In other words, for example, the operation information transmitted by the subject response device 2-1 is received by the corresponding earphone 1-1, but not received by the main body 3 and the other earphones 1-2 to 1-5. Then, the voltage information transmitted by the subject response device 2-1 is received by the corresponding earphone 1-1 and the main body 3, and not received by the other earphones 1-2 to 1-5. Further, for example, the voltage information transmitted by the subject response device 2-1 may be received not by the main body 3 but only by the earphone 1-1.

For example, the subject response device 2-*i* and the earphone 1-*i* of the test device Di performs the wireless communication in a specific time slot different from the other test device among a predetermined number of time slots which form one frame in the time division multiplexing system. Then, the earphone 1-*i* presents the test sound to the subject with the wireless communication, and acquires the operation information of the subject with respect to the corresponding subject response device 2-*i* from the subject response device 2-*i*.

Further, the wireless communication between the main body 3, the earphone 1-*i*, and the subject response device 2-*i* in the second embodiment may be performed in the time division multiplexing method described in JP 6126289 B1 for example.

In the second embodiment, the main body 3 uses the wireless communication with the earphone 1-*i* to perform the following operations of:

(a) transmitting an examination start command to the earphone 1-*i*, and (b) receiving an examination result from the earphone 1-*i* after the audiometry in the test device Di is completed.

When receiving the examination start command, the earphone 1-*i* sequentially presents the plurality of test sounds to the subject according to the automatic audiometry program. Then, the earphone 1-*i* specifies an examination result on the basis of the operation information acquired from the subject response device 2-*i*. Then, after the audiometry is completed, the specified examination result is transmitted by the earphone 1-*i*. For example, the automatic audiometry such as an automatic threshold test or an automatic screening test is performed according to the automatic audiometry program.

In the automatic audiometry, while the test sound is not presented by the earphone portion (the right earphone portion 11R or the left earphone portion 11L), which to be selected for presenting the test sound, the main controller 42 of the earphone 1-*i* causes the light-emitter of the selected earphone portion (the right light-emitter 13R or the left light-emitter 13L) to emit light in a mode different from a manual audiometry (here, purple instead of white). In addition, while there is no response from the subject in the automatic audiometry, the main controller 42 of the earphone 1-*i* causes the light-emitter (the right light-emitter 13R or the left light-emitter 13L) of the unselected earphone portion, which does not present the test sound, to emit light in a mode different from the manual audiometry (here, purple instead of white).

Further, when the automatic audiometry is completed, the main controller 42 of the earphone 1-*i* causes at least one of the right light-emitter 13R and the left light-emitter 13L to emit light in a different mode (here, sky blue).

As described above, according to the second embodiment, even when the progress status of the examinations on the plural subjects (the test devices Di) varies in the automatic audiometry, the examiner can visually check the emitting states of the right light-emitter 13R and the left light-emitter 13L with an almost fixed line of sight while looking at the state of each subject. Therefore, the examiner easily monitors the progress of audiometry of plural subjects.

Third Embodiment

The earphone 1-*i* of the audiometer according to a third embodiment further includes a microphone for measuring an environmental noise. Further, the microphone is disposed in the vicinity (for example, a sound output side) of the speakers 12L and 12R in the inner portion of the casings 10L and 10R for example. In addition, the microphone can be used even to check the output of the test sound from the speakers 12L and 12R.

In the third embodiment, the main controller 42 of the earphone 1-*i* performs the following operations of:

(a) acquiring the output signal of the microphone and specifying the level of the environmental noise on the basis of the output signal, and (b) causing the light-emitter (the right light-emitter 13R or the left light-emitter corresponding to an earphone portion selected as the earphone portion for presenting the test sound to emit light in a mode in accordance with the level of the environmental noise measured by the microphone when the environmental noise is measured.

Here, the main controller 42 makes the of the earphone portion for presenting the test sound light with a color in accordance with the level of the environmental noise. For example, the main controller 42 makes the light-emitter of the earphone portion for presenting the test sound light with a green color in a case where the level of the environmental noise is in a first range, yellow in a case where the level of the environmental noise is in a second range lower than the first range, and red in a case where the level of the environmental noise is in a third range lower than the second range.

For example, when an environmental noise measurement mode is selected on the basis of an operation of the examiner, as described above, the main controller 42 causes the light-emitter of the earphone portion for presenting the test sound to emit light in a mode in accordance with the level of the environmental noise measured by the microphone. On the other hand, when an audiometry mode is selected on the basis of the operation of the examiner, the main controller 42 causes the light-emitter of the earphone portion for presenting the test sound to emit light in a mode in accordance with the level of the test sound as described in the first and second embodiments.

Further, the environmental noise measurement mode and the audiometry measurement mode may be selected on the basis of the operation on the earphone 1-*i*, or may be selected on the basis of a command from the main body 3.

Further, other configurations and operations of the audiometer according to the third embodiment are similar to those of the first or second embodiment, and the description thereof will be omitted.

As described above, according to the third embodiment, the environmental noise is measured by the earphone 1-*i* as needed, and the examiner can visually check the measurement result. In addition, in a case where the audiometry of plural subjects is performed in parallel, the level of the environmental noise may be different according to positions of the plural subjects. However, the environmental noise is measured by the earphone 1-*i* which is worn by each of the plural subjects. Therefore, the level of the environmental noise of each subject is accurately measured.

Further, to a person skilled in the art, various alterations and modifications of the above-described embodiments are obvious. Such alterations and modifications may be carried out without departing from the spirit and scope of the subject matter and without affecting the intended merits. In other words, in the present disclosure, such alterations and modifications are meant to be encompassed by the claims.

For example, in the first to third embodiments, the right light-emitter 13R and the left light-emitter 13L are provided in the left earphone portion 11L and the right earphone portion 11R, respectively. However, the right light-emitter 13R and the left light-emitter 13L each may be provided in the headband portion to be adjacent to the left earphone portion 11L and the right earphone portion 11R.

In addition, in the first to third embodiments, the main controller 42 causes the right light-emitter 13R and the left light-emitter 13L to emit light (light or blinking) in a different color in accordance with a plurality of modes using RGB color LEDs. However, instead of the above configuration, the main controller 42 may make the right light-emitter 13R and the left light-emitter 13L blinking in a different blinking pattern in accordance with a plurality of modes of a single-color LED.

Further, the first to third embodiments have been described about the wireless audiometer, but the present disclosure may be applied to a wired of audiometer.

Further, in the first to third embodiments, when an incident of error such as a voltage reduction of the battery, a disconnection of communication link, or an start error is detected, the main controller 42 may cause the right light-emitter 13R and the left light-emitter 13L to emit light in a mode in accordance with a type of the incident of error.

Further, in the first to third embodiments, a bone conduction earphone and an acceleration sensor may be provided in the earphone 1-*i* in addition to the earphone portions 11L and 11R as an air conduction earphone. In this case, when an error of the bone conduction earphone is detected on the basis of the output signal of the acceleration sensor, the right light-emitter 13R and the left light-emitter 13L may emit light in a mode corresponding to the error.

Further, in the third embodiment, the microphone for measuring the environmental noise may be used as a monitor of the test sound. In this case, in an audiometry mode, when an incident of error such as a level error of the test sound or a failure to present the test sound is detected the right light-emitter 13R and the left light-emitter 13L may emit light in a mode in accordance with the type of the abnormal event.

The earphone for an audiometer of the present disclosure may be any one of the following first to fourth earphones for an audiometer.

The first earphone for an audiometer includes a right earphone portion, a left earphone portion, a right light-emitter corresponding to the right earphone portion, a left light-emitter corresponding to the left earphone portion, and a controller which selects an earphone portion to output a test sound from the right earphone portion and the left earphone portion, and causes the right light-emitter or the left light-emitter corresponding to the selected earphone portion to emit light in a mode in accordance with the test sound.

The second earphone for an audiometer according to the earphone for the first audiometer is configured such that the controller causes the right light-emitter or the left light-emitter corresponding to the unselected earphone portion to emit light in a mode different from the mode in accordance with the test sound when a response operation with respect to the test sound is detected.

The third earphone for an audiometer according to the earphone for the first or second audiometer further includes a microphone which measures a sound pressure of the earphone portion, wherein the controller causes the right light-emitter or the left light-emitter corresponding to the selected earphone portion to emit light in a mode in accordance with the sound pressure measured by the microphone.

The fourth earphone for an audiometer according to the earphones for any one of the first to third audiometers is configured such that the right light-emitter includes a right light-emitting element provided in a right hook portion of the right earphone portion, and the left light-emitter includes a left light-emitting element provided in a left hook portion of the left earphone portion.

The audiometer of the present disclosure may include any one of the first to fourth earphones for an audiometer, and a main body which causes the earphone for an audiometer to output the test sound.

The present disclosure is applicable to a wireless audiometer which performs the audiometry on plural subjects in parallel for example.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An earphone for an audiometer, comprising:
a right earphone portion;
a left earphone portion;
a right light-emitter corresponding to the right earphone portion;
a left light-emitter corresponding to the left earphone portion; and
a controller,
wherein the controller selects any one of the right earphone portion and the left earphone portion as an earphone portion for presenting a test sound, and causes the light-emitter corresponding to the selected earphone portion to emit light in a mode in accordance with the test sound, and
the controller causes a light-emitter corresponding to the unselected earphone portion to emit light in a mode different from the mode in accordance with the test sound when a response to the test sound by a subject is detected.

2. The earphone for an audiometer according to claim 1, further comprising:
a microphone which measures a sound pressure of the earphone portion,
wherein the controller causes the light-emitter corresponding to the selected earphone portion to emit light in a mode in accordance with the sound pressure measured by the microphone.

3. The earphone for an audiometer according to claim 1,
wherein the right light-emitter includes a right light-emitting element which is provided in a right hook portion of the right earphone portion, and
wherein the left light-emitter includes a left light-emitting element which is provided in a left hook portion of the left earphone portion.

4. An audiometer, comprising:
the earphone for an audiometer according to claim 1; and
a main body which causes the earphone for an audiometer to present the test sound.

5. An audiometer, comprising:
the earphone for an audiometer according to claim 2; and
a main body which causes the earphone for an audiometer to present the test sound.

6. An audiometer, comprising:
the earphone for an audiometer according to claim 3; and
a main body which causes the earphone for an audiometer to present the test sound.

* * * * *